(12) United States Patent
Arruda et al.

(10) Patent No.: US 8,338,664 B2
(45) Date of Patent: Dec. 25, 2012

(54) NUCLEIC ACID MOLECULES ENCODING PLANT PROTEINS IN THE C3HC4 FAMILY AND METHODS FOR THE ALTERATION OF PLANT CELLULOSE AND LIGNIN CONTENT

(75) Inventors: Paulo Arruda, Campinas (BR); Isabel Rodrigues Gerhardt, Campinas (BR)

(73) Assignee: Monsanto Do Brasil LTDA., Sao Paulo (BR)

( * ) Notice: Subject to any disclaimer, the term of this patent is extended or adjusted under 35 U.S.C. 154(b) by 498 days.

(21) Appl. No.: 12/520,266

(22) PCT Filed: Dec. 20, 2007

(86) PCT No.: PCT/BR2007/000358
§ 371 (c)(1),
(2), (4) Date: Dec. 2, 2009

(87) PCT Pub. No.: WO2008/074116
PCT Pub. Date: Jun. 26, 2008

(65) Prior Publication Data
US 2010/0077509 A1  Mar. 25, 2010

Related U.S. Application Data

(60) Provisional application No. 60/871,061, filed on Dec. 20, 2006.

(51) Int. Cl.
| | |
|---|---|
| *A01H 5/00* | (2006.01) |
| *C12N 15/82* | (2006.01) |
| *C12N 15/11* | (2006.01) |
| *C07K 14/415* | (2006.01) |

(52) U.S. Cl. ....... 800/284; 800/298; 530/370; 536/23.1; 435/91.1; 435/468; 435/419; 435/320.1

(58) Field of Classification Search .................. None
See application file for complete search history.

(56) References Cited

U.S. PATENT DOCUMENTS

2008/0196125 A1 * 8/2008 Papes et al. ................ 800/298

FOREIGN PATENT DOCUMENTS

| WO | WO 2004/048595 A2 | | 6/2004 |
|---|---|---|---|
| WO | WO 2005/001051 | * | 1/2005 |
| WO | WO 2005/001051 A2 | | 1/2005 |
| WO | WO 2005/096805 A2 | | 10/2005 |

OTHER PUBLICATIONS

Guo et al (PNAS 2004 (101)25,9205-9210).*
Inter-ProScan Results, ran on Jan. 10, 2012.*
Richmond et al (Plant Physiology, Oct. 2000, vol. 124, pp. 495-498).*
Ma et al (Gene, vol. 444, Issues 1-2, 2009, 33-45).*
International Search Report PCT/BR2007/000358 dated May 8, 2008.

* cited by examiner

*Primary Examiner* — Brent T Page
*Assistant Examiner* — Lee A Visone
(74) *Attorney, Agent, or Firm* — Thompson Coburn LLP

(57) ABSTRACT

Polynucleotides, nucleic acid constructs, and methods are disclosed for the modification of cellulose and/or lignin content in plant tissues. Plants are genetically engineered with a gene encoding a C3HC4 protein, which leads to increased cellulose content when over-expressed in the plant vascular system. Plant transformants harboring the C3HC4 protein gene show increased content of cellulose and/or decreased lignin content, traits that are thought to improve hardwood trees for cellulose extraction during pulping and papermaking.

24 Claims, 7 Drawing Sheets

NUCLEIC ACID MOLECULES ENCODING PLANT PROTEINS IN THE C3HC4 FAMILY AND METHODS FOR THE ALTERATION OF PLANT CELLULOSE AND LIGNIN CONTENT

CROSS-REFERENCE TO RELATED APPLICATION

This application claims priority to U.S. Provisional Application No. 60/871,061, filed Dec. 20, 2006, the disclosure of which is incorporated by reference in its entirety.

FIELD OF THE INVENTION

The present invention relates to the field of plant biotechnology. More specifically, this invention relates to alteration of cellulose content by regulating expression of genes encoding C3HC4 proteins.

BACKGROUND OF THE INVENTION

During wood formation in higher plants, most glucose produced during carbohydrate metabolism is channeled to cellulose for secondary wall deposition. Djerbi et al., *Cellulose* 11: 301-12 (2004). Cellulose is a fibrous polymer consisting of linear chains of β-(1,4)-linked glucan molecules that crystallize to form microfibrils. Microfibrils impart the characteristic flexible strength of cellulose. Cellulose is synthesized in higher plants by large multimeric plasma membrane-bound complexes that form rosette structures at the ends of microfibrils. Somerville, *Ann. Rev. Cell Dev. Biol.* 22: 53-78 (2006).

Cellulose is valuable as pulp, as fiber, and as a starting point for the synthesis of commercially important polymers. Alterations to increase cellulose deposition are likely to have a repressive effect on lignin deposition. Hu et al., *Nature Biotech.* 17: 808-19 (1999). A reduction in lignin content in woody plants is desirable, as the industrial production of cellulose and chemical removal of lignin is costly and represents an enormous environmental challenge.

The biosynthesis pathway of cellulose is poorly understood at the molecular level. Genes from the cellulose synthase (CESA) family, and those encoding proteins for N-glycan synthesis and processing have been isolated in a large number of organisms. Nicol et al., *EMBO J.* 17: 5562-76 (1998).

An experimental system largely used to study wood formation, especially cellulose synthesis and deposition, consists in bending a wood tree so that tension wood (TW) is formed at the tension side of the stem. Andersson-Gunneras et al., *Plant J.* 45: 144-65 (2006). In *Eucalyptus* and *Populus* species, tension wood occurs typically on the upper side of leaning stems and allows the tree to reorient its axis. Tension wood is mainly characterized by xylem fibers with an extra thick gelatinous secondary layer (G layer) in their lumen. This G layer contains almost exclusively cellulose microfibrils with high crystallinity. Déejardin et al., *Plant Biol.* 6: 55-64 (2004). Because tension wood is enriched in cellulose but is deficient in lignin and hemicelluloses, it may be used to detect and analyze genes involved in the control of carbon flow into lignin, cellulose, and hemicellulose.

Andersson-Gunneras et al. (2006) identified genes highly expressed in TW that are involved in cell wall formation, such as genes involved in carbohydrate metabolism and cytoskeleton formation, as well as housekeeping genes and two genes with unknown function in *Populus tremula* (L.)×*P. tremuloides* (Michx). A C3HC4-type zinc-finger (RING finger) protein showed differential expression TW, but there are no data, in this study or in others, implicating its role in cellulose biosynthesis.

Zinc finger domains are relatively small protein motifs that bind one or more zinc atoms. They were first identified as a DNA-binding motif in transcription factor TFIIIA from *Xenopus laevis*, however they are now recognized to bind DNA, RNA, protein and/or lipid substrates. The RING-finger is a specialized type of Zn-finger of 40 to 60 residues that binds two atoms of zinc, and is probably involved in mediating protein-protein interactions. There are two different variants, the C3HC4-type and a C3H2C3-type. The C3HC4-type RING finger motif is found in a number of cellular and viral proteins, some of which have been shown to have ubiquitin E3 ligase activity both in vivo and in vitro. Laity et al., *Curr. Opin. Struct. Biol.* 11:39-46 (2001).

Considering the difficulties associated with traditional forest tree breeding, such as the slow progress due to their long generation periods and the difficulty of producing a plant with a desirable trait, developments in gene technology can reduce significantly the time required to produce a new variety of plant and allow closer targeting of traits considered desirable by the forest and pulp industries in specific trees species.

SUMMARY OF THE INVENTION

In one aspect, the invention provides n isolated nucleic acid sequence comprising a sequence selected from the group consisting of: (a) a nucleic acid sequence set forth in SEQ ID NO: 1, or the complement strand thereof; (b) a nucleic acid sequence encoding the amino acid sequence set forth in SEQ ID NO: 2; (c) a nucleic acid sequence capable of hybridizing under stringent conditions with a nucleic acid sequence of (a) or (b), wherein said hybridizing sequence encodes a C3HC4 polypeptide; (d) a nucleic acid which is an allelic variant or alternative splice variant of the nucleic acid sequence of (a) or (b); and (e) a nucleic acid sequence which has at least 50%, 60%, 70%, 75%, 80%, 85%, 90% or more sequence identity to the sequence of (a) or (b).

In another aspect, the invention provides an isolated C3HC4 protein selected from the group consisting of: (a) a polypeptide set forth in SEQ ID NO 2; (b) a polypeptide with an amino acid sequence having at least 85% or more sequence identity to the amino acid sequence set forth in SEQ ID NO 2; and (c) a variant of a polypeptide as defined in (a) or (b).

In another aspect, the invention provides a nucleic acid construct comprising an isolated C3HC4 polynucleotide sequence operably linked to one or more suitable promoters that drive the expression of the C3HC4 polynucleotide sequence. In one embodiment, a plant cell comprises the nucleic acid construct. In a further embodiment, a transgenic plant is generated from the plant cell and the plant has altered cellulose and/or lignin content compared to a non-transgenic plant of the same species. In still further embodiments, the plant is a dicotyledon, monocotyledon, gymnosperm, or hardwood tree. Further embodiments include progeny of the transgenic plant, including hybrid plants.

In another aspect, the invention provides a method for altering the cellulose and/or lignin content in a plant, comprising (a) introducing into an isolated plant cell a nucleic acid construct comprising an isolated C3HC4 polynucleotide sequence, operably linked to one or more suitable promoters that drive the expression of the C3HC4 polynucleotide sequence; and (b) culturing said plant cell under conditions that promote growth of a plant, wherein said plant over-expresses the C3HC4 protein and has increased cellulose and/or reduced lignin content compared to a non-transgenic plant of the same species.

DETAILED DESCRIPTION OF THE INVENTION

Figure 1:
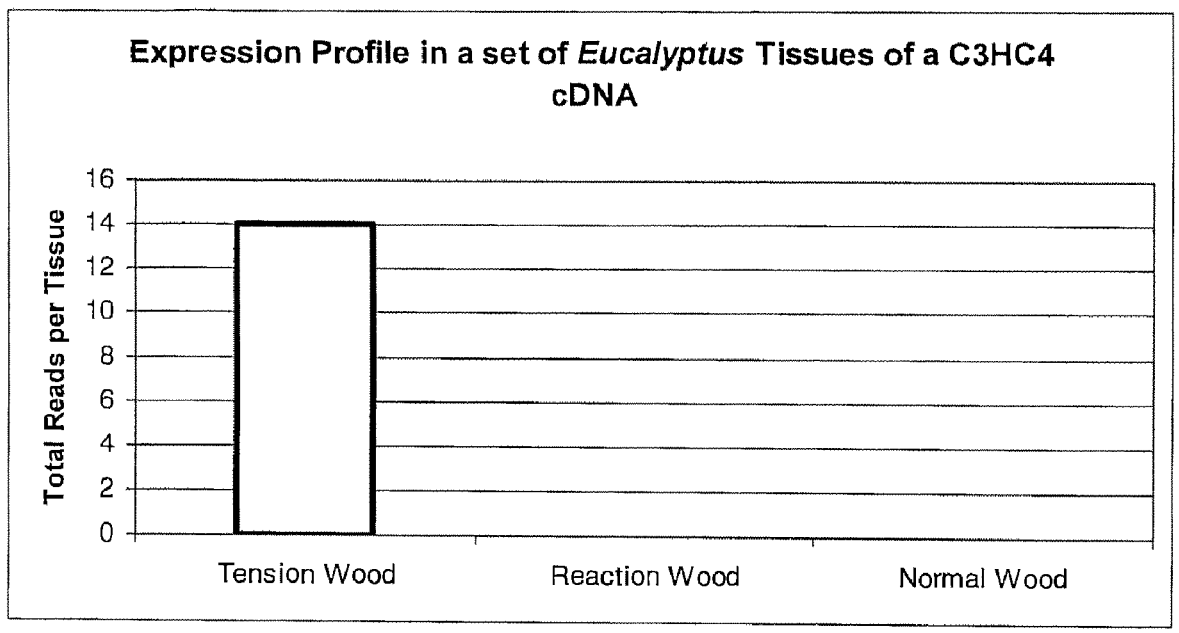
FIG. 1 shows the expression profile in a set of *Eucalyptus* tissues of a C3HC4 cDNA. An orthologous gene was cloned from mRNA isolated from the xylem of *Populus deltoides*.

The present invention concerns genetically manipulated plants that are characterized by an increased expression of the C3HC4 protein. In this regard, the invention focuses on genetically manipulated plants that overexpress a nucleic acid molecule comprising C3HC4 gene, thereby modulating the cellulose content of said genetically manipulated plant. Increasing the rate of transcription of a gene may result in the enhancement of the protein product, thereby enhancing the rate of the metabolic process in which this gene is involved.

In this regard, the present inventors have determined that genetically manipulated plants that overexpress a C3CH4 gene display increased cellulose content. Thus, the inventors determined that the C3HC4 protein controls, directly or indirectly, gene(s) and/or protein(s) related to cellulose synthesis.

As such, applications of the invention include but are not limited to the improvement of cellulose fiber production, during papermaking, through increased cellulose content in woody trees, and the improvement of cellulose fiber extraction for the production of textiles through the increase of cellulose content in cotton fibers. Additionally, enhanced deposition of cellulose is likely to have a repressive effect on lignin deposition. Industrial production of cellulose from woody trees requires the chemical removal of lignin during the pulping process, which makes use of large amounts of concentrated chemicals. For high-quality paper production, residual lignin needs to be further removed by an additional bleaching step involving the use of extremely hazardous substances. The overall process is costly and represents an enormous environmental challenge. For this reason, reducing lignin content in woody plants, typically trees, is expected to lessen the chemical and energy demands of these highly expensive extraction processes, and it also should reduce the amount of effluent material, a major potential environmental pollutant that is both difficult and expensive to process. Campbell et al., *Plant Physiol.* 110: 3-13 (1996). Thus, genetic engineering of cellulose biosynthesis can provide a strategy to augment cellulose quality and quantity, while reducing lignin content in transgenic plants.

Technical terminology in this description conforms to common usage in biochemistry, molecular biology, and agriculture. This usage and these technical terms are explicated in: MOLECULAR CLONING: A LABORATORY MANUAL (3rd ed.), vol. 1-3, Cold Spring Harbor Laboratory Press (2001); CURRENT PROTOCOLS IN MOLECULAR BIOLOGY, Greene Publishing Associates and Wiley-Interscience (1988), with periodic updates; SHORT PROTOCOLS IN MOLECULAR BIOLOGY: A COMPENDIUM OF METHODS FROM CURRENT PROTOCOLS IN MOLECULAR BIOLOGY ($5^{th}$ ed.), vol. 1-2, John Wiley & Sons, Inc. (2002); GENOME ANALYSIS: A LABORATORY MANUAL, vol. 1-2, Cold Spring Harbor Laboratory Press (1997). Suitable plant biology techniques, as described here, are further explicated in methodology treatises such as METHODS IN PLANT MOLECULAR BIOLOGY: A LABORATORY COURSE MANUAL, Cold Spring Harbor Laboratory Press (1995). Various methods employing PCR are described, e.g., in Innis et al., PCR PROTOCOLS: A GUIDE TO METHODS AND APPLICATIONS, Academic Press (1990), and in Dieffenbach and Dveksler, PCR PRIMER: A LABORATORY MANUAL ($2^{nd}$ ed.), Cold Spring Harbor Laboratory Press (2003). PCR-primer pairs can be derived from known sequences by known techniques such as using computer programs intended for that purpose, such as Primer, Version 0.5, 1991 (Whitehead Institute for Biomedical Research, Cambridge, Mass.). Illustrative methodology for chemical synthesis of nucleic acids is discussed, for example, in Beaucage and Caruthers, *Tetra. Letts.* 22: 1859-62 (1981), and Matteucci and Caruthers, *J. Am. Chem. Soc.* 103: 3185 (1981).

Restriction enzyme digestions, phosphorylations, ligations and transformations were done as described in Sambrook et al., MOLECULAR CLONING: A LABORATORY MANUAL ($2^{nd}$ ed.), Cold Spring Harbor Laboratory Press (1989). All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. It is therefore understood that modifications in the DNA sequence encoding C3HC4 protein which do not substantially affect the functional properties of the protein are contemplated.

In this description, "expression" denotes the production of the protein product or polypeptide encoded by a gene. Alternatively or additionally, "expression" denotes the combination of intracellular processes, including transcription and translation, undergone by a coding DNA molecule such as a structural gene to produce a polypeptide. "Over-expression" refers to the expression of a particular gene sequence in which the production of mRNA or polypeptide in a transgenic organism exceeds the levels of production in non-transgenic organism.

The term "heterologous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

In contrast, the term "endogenous nucleic acid" refers to a nucleic acid, gene, polynucleotide, DNA, RNA, mRNA, or cDNA molecule that is present in a plant or organism that is to be genetically engineered. An endogenous sequence is "native" to, i.e., indigenous to, the plant or organism that is to be genetically engineered.

The term "homologous sequences" refers to polynucleotide or polypeptide sequences that are similar due to common ancestry and sequence conservation.

For the purposes of this invention, "paralogs" are homologs produced by gene duplication. They represent genes derived from a common ancestral gene that duplicated within an organism and then subsequently diverged. "Orthologs" are homologs produced by speciation. They represent genes derived from a common ancestor that diverged due to divergence of the organisms with which they are associated. See Brinkman and Leipe, In: BIOINFORMATICS, A PRACTICAL GUIDE TO THE ANALYSIS OF GENES AND PROTEINS 323-58, Wiley-Interscience (2001).

The term "functional homolog" refers to a polynucleotide or polypeptide sequences that are similar due to common ancestry and sequence conservation and have identical or similar function at the catalytic, cellular, or organismal levels.

C3HC4 Sequences

Many of the biological processes necessary for the metabolism and development on an organism are governed by gene families. This is the case for the C3HC4 protein, which belongs to a gene family comprising many genes. The C3HC4-domain proteins belong to the so-called "zinc finger" family of proteins, characterized by the "RING finger" domain, which comprises eight metal ligands formed by the consensus motif, C3HC4. RING finger domains usually bind two zinc ions in a unique cross brace arrangement and can basically be considered a protein-interaction domain. Jackson et al., Trends Cell Biol. 10: 429-39 (2000).

RING-finger proteins have been implicated in a range of diverse biological processes, from transcriptional and translational regulation to development and targeted proteolysis. Accordingly, other C3HC4 family members would also enhance cellulose content. An illustrative C3HC4 gene set forth in SEQ ID NO:1 was isolated from poplar.

It is expected that any gene from any organism encoding a RING finger gene, encoding a protein with a structure and biological properties similar to the translation product of a C3HC4 gene will have the same effect on cellulose content as the inventors have demonstrated for transgenic plants as described in the examples, supra. These genes can be identified and functionally annotated by sequence comparison. A knowledgeable molecular biologist can readily identify a sequence related to the C3HC4 sequence with the aid of conventional methodology, such as screening cDNA or genomic libraries with suitable hybridization probes or searching public databases, such as NCBI's Genbank. Homologous sequences also can be isolated with the aid of degenerate oligonucleotides, using known PCR-based techniques.

It also is possible to use computational programs that empower various known techniques for identifying genes by sequence comparison. Exemplary techniques in this regard are described, for instance, by Innis et al., PCR PROTOCOLS: A GUIDE TO METHODS AND APPLICATIONS, Academic Press (1990), and in GENOME ANALYSIS: A LABORATORY MANUAL, volumes 1 and 2, Cold Spring Harbor Laboratory Press (1997).

In their investigations relating to this invention, the present inventors induced TW in plants of an interspecific hybrid, E. grandis×E. urophylla. A number of genes differentially expressed between TW and normal wood thus were identified. Among the genes that have their expression altered in tension wood, a number were determined to code for a member of the C3HC4-type zinc finger family, which is highly expressed in Eucalyptus TW.

Because a member of the C3HC4 protein family is highly expressed in TW, a tissue consisted mainly of highly crystalline cellulose, and C3HC4 members seem to be involved in the control of the vascular meristem and secondary growth, it might be expected that genetic transformation of woody trees with nucleic acid constructs, comprising molecules encoding members of the C3HC4 family, would alter vascular patterning and cellulose synthesis and deposition. Thus, an increase in cellulose synthesis and deposition would occur when a C3HC4 gene is over-expressed. Conversely, where a C3HC4 gene is down-regulated, the inventors anticipate a decrease in cellulose synthesis. Since alteration in cellulose synthesis and deposition, in general, produces alteration in lignin synthesis and deposition, see Hu et al., Nature Biotech. 17: 808-19 (1999), the inventors likewise understood that increasing cellulose synthesis and deposition would decrease the lignin content of the wood tree. The opposite scenario would pertain, if the cellulose synthesis were reduced.

In the context of the present invention, a sequence can be identified by methodology as described above, and thereby functionally annotated as belonging to the C3HC4 family. In this description, the phrases "C3HC4 polynucleotide sequence" and "C3HC4 nucleic acid sequence" denote any nucleic acid, gene, polynucleotide, DNA, RNA, mRNA, cDNA molecule that encodes for a C3HC4 polypeptide that, when over-expressed, results in an increase in the cellulose content and/or in a decrease in the lignin content of a plant The phrases "C3HC4 polynucleotide sequence" and "C3HC4 nucleic acid sequence" also encompass any nucleic acid molecule with a nucleotide sequence capable of hybridizing, under stringent conditions, with any of the sequences described herein and that codes for a C3HC4 polypeptide that, when over-expressed, results in an increase in the cellulose content and/or in a decrease in the lignin content of a plant. The phrases also connote sequences that cross-hybridize with SEQ ID NO:1, preferably having at least 40%, more preferably at least 60%, even more preferably at least 80%, and most preferably at least 90% homology or identity with SEQ ID NO.: 1.

A nucleotide sequence of the invention also may encode a protein that is homologous to the predicted gene product set forth in SEQ ID NO: 2.

Also contemplated by the phrases "C3HC4 polynucleotide sequence" and "C3HC4 nucleic acid sequence" denote those sequences represented by fragments or variants of SEQ ID NO: 1 that share at least 50%, preferably at least 60%, more preferably at least 70%, even more preferably at least 80%, and most preferably at least 90% identity with SEQ ID NO: 1 and code for C3HC4 polypeptides that, when over-expressed, results in an increase in the cellulose content and/or in a decrease in the lignin content of a plant. By the same token, the nucleotide sequences of the invention include those sequences that encode for polypeptides that comprise an amino acid sequence of SEQ ID NO: 2 or an amino acid sequence which is at least 50%, preferably at least 60%, more preferably at least 70%, even more preferably at least 80%, and most preferably at least 90% identical to SEQ ID NO: 2, the over-expression of which results in an increase in the cellulose content and/or in a decrease in the lignin content of a plant.

The phrase "stringent conditions" here connotes parameters with which the art is familiar. Single-stranded polynucleotides hybridize when they associate based on a variety of well-characterized physicochemical forces, such as hydrogen bonding, solvent exclusion, and base stacking. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number). One with ordinary skill in the art can readily select such conditions by varying the temperature during the hybridization reaction and washing process, the salt concentration during the hybridization reaction and washing process, and so forth.

For hybridization of complementary nucleic acids, which have more than 100 complementary residues, on a filter in a Southern or Northern blot, "stringent" hybridization conditions are exemplified by a temperature that is about 5° C. to 20° C. lower than the thermal melting point (Tm) for the specific sequence, at a defined ionic strength and pH. The Tm is the temperature, under defined ionic strength and pH, at which 50% of the target sequence hybridizes to a perfectly matched probe. Nucleic acid molecules that hybridize under stringent conditions typically will hybridize to a probe based on either the entire cDNA or selected portions. More preferably, "stringent conditions" here refers to parameters with which the art is familiar, such as hybridization in 3.5×SSC, 1×Denhardt's solution, 25 mM sodium phosphate buffer (pH 7.0), 0.5% SDS, and 2 mM EDTA for 18 hours at 65° C., followed by 4 washes of the filter at 65° C. for 20 minutes, in 2×SSC, 0.1% SDS, and a final wash for up to 20 minutes in 0.5×SSC, 0.1% SDS, or 0.3×SSC and 0.1% SDS for greater stringency, and 0.1×SSC, 0.1% SDS for even greater stringency. Other conditions may be substituted, as long as the degree of stringency in substantially equal to that provided here, using a 0.5×SSC final wash.

As noted, the phrase "C3HC4 nucleic acid sequence" in this description refers to any nucleic acid molecule with a nucleotide sequence capable of hybridizing under stringent conditions with the sequence disclosed herein, and coding for a polypeptide equivalent to the protein having the amino acid sequence disclosed herein as SEQ ID NO.: 2. The phrase also includes sequences which cross-hybridize with SEQ ID NO.: 1, preferably having at least 55%, preferably at least 65%, more preferably at least 75%, even more preferably at least 85%, and most preferably at least 90% identical to homology or identity with SEQ ID NO: 1. The nucleotide sequence of the invention may encode a protein that is homologous to the predicted gene product of SEQ ID NO: 2.

Further embodiments include any nucleic acid molecule comprising any of the above base sequences with one or more bases deleted, substituted, inserted, or added, and coding for a polypeptide which is homologous to the protein encoded by SEQ ID NO: 2. Such nucleic acid molecules include allelic variants and alternative splice variants of SEQ ID NO: 1.

Accordingly, the term "variant" is a nucleotide or amino acid sequence that deviates from the standard, or given, nucleotide or amino acid sequence of a particular gene or protein.

The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, Md.) software. "Variant" may also refer to a "shuffled gene," as described, for example, in U.S. Pat. No. 6,506,603, No. 6,132,970, No. 6,165,793 and No. 6,117,679.

The "base sequences with one or more bases deleted, substituted, inserted, or added" referred to here are widely known by those having ordinary skill in the art to retain physiological activity even when the amino acid sequence of a protein generally having that physiological activity has one or more amino acids substituted, deleted, inserted, or added. Nucleotide sequences that have such modifications and that code for the C3HC4 protein are included within the scope of the present invention. For example, the poly A tail or 5'- or 3'-end non-translated regions may be deleted, and bases may be deleted to the extent that amino acids are deleted. Bases may also be substituted, as long as no frame shifts results. Bases may also be "added" to the extent that amino acids are added. However, it is essential that such modifications do not result in the loss of C3HC4 protein function. Such modified nucleic acids can be obtained, for example, by modifying the base sequences of the invention so that amino acids at specific sites are substituted, deleted, inserted, or added by site-specific mutagenesis. See Zoller and Smith, *Nucleic Acid Res.* 10: 6487-500 (1982).

It is understood that amino acid and nucleic acid sequences may include additional residues, such as additional N- or C-terminal amino acids or 5' or 3' sequences. Such additions are suitable as long as the resultant sequence codes for a polypeptide maintaining the same or equivalent biological protein activity.

The present invention provides a nucleotide sequence encoding the C3HC4 protein. This sequence may be derived from cDNA, such as *Populus deltoides* cDNA or from genomic DNA. An exemplary cDNA clone is set forth as SEQ ID NO: 1, supra., which encodes a C3HC4 protein. Pursuant to an aspect of the invention, one modifies the content of cellulose in plant tissues, such as fiber cells of woody xylem or cotton seeds, by controlling the expression of the C3HC4 protein. Accordingly, plant cells or whole plants are genetically engineered, for example, with the C3HC4 protein coding sequence from, for instance, *Populus deltoides* which is expressed preferably in fiber cells and causes an increase in cellulose synthesis and deposition.

Additionally, the invention provides a nucleic acid molecule comprising a nucleotide sequence selected from (a) SEQ. ID. No.: 1, or a part thereof, or a complement thereof; (b) a nucleotide sequence that hybridizes to said nucleotide sequence of (a) under a wash stringency equivalent to 0.1× SSC to 1.0×SSC, 0.1% SDS, at 50-65° C., (c) a nucleotide sequence encoding a protein having the same amino acid sequence as is encoded by the nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code.

A further feature of the invention are proteins and polypeptides encoded by the nucleic acid molecule of the invention, exemplified by, but not being limited to, the polypeptide which has the amino acid sequences comprised of SEQ ID. NO.: 2. Preferably, the polypeptides of the invention have amino acid sequences, which contain regions that are at least 60% identical to the sequences referred to above. Identity greater than 70% is preferred, while identity greater than 80%, 90% or even 95% with respect to sequence above is most preferred.

The nucleic acid molecule of the invention may be used "neat", or preferably in expression vector constructs, for introducing into cells, such as plant cells. Standard molecular biological techniques, well known to the skilled artisan, may be used.

Nucleic Acid Constructs

Recombinant nucleic acid constructs may be made using standard techniques. For example, a nucleotide sequence for transcription may be obtained by treating a vector containing said sequence with restriction enzymes to cut out the appropriate segment. The nucleotide sequence for transcription may also be generated by annealing and ligating synthetic oligonucleotides or by using synthetic oligonucleotides in a polymerase chain reaction (PCR) to give suitable restriction sites at each end. The nucleotide sequence then is cloned into a vector containing suitable regulatory elements, such as upstream promoter and downstream terminator sequences. Typically, plant transformation vectors include one or more cloned plant coding sequence (genomic or cDNA) under the transcriptional control of 5' and 3' regulatory sequences, and a selectable marker. Such plant transformation vectors typically also contain a promoter, a transcription initiation start site, an RNA processing signal (such as splicing signal sequences), a transcription termination site, and/or a polyadenylation signal. Enhancers and targeting sequences may also be present.

Suitable constitutive plant promoters which can be useful for expressing the C3HC4 protein sequences include but are not limited to the cauliflower mosaic virus (CaMV) 35S promoter, the maize and the *Populus* polyubiquitin promoters, which confer constitutive, high-level expression in most plant tissues (see, e.g., WO 2007/00611, U.S. Pat. No. 5,510,474; Odell et al., *Nature,* 1985, 313: 810-812); the nopaline synthase promoter (An et al., 1988, *Plant Physiol.* 88: 547-552); the FMV promoter from figwort mosaic virus (U.S. Pat. No. 5,378,619); and the octopine synthase promoter (Fromm et al., 1989, *Plant Cell* 1: 977-984).

The vector may also contain termination sequences, which are positioned downstream of the nucleic acid molecules of the invention, such that transcription of mRNA is terminated, and polyA sequences added. Exemplary terminators are the cauliflower mosaic virus (CaMV) 35S terminator and the nopaline synthase gene (NOS) terminator.

Expression vectors may also contain a selection marker by which transformed cells can be identified in culture. The marker may be associated with the heterologous nucleic acid molecule, i.e., the gene operably linked to a promoter. As used herein, "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3'-O-phosphotransferase (kanamycin, neomycin and G418 resistance). These markers may include resistance to G418, hygromycin, bleomycin, kanamycin, and gentamicin. The construct also may contain the selectable marker gene Bar, which confers resistance to herbicidal phosphinothricin analogs like ammonium gluphosinate. Thompson et al., *EMBO J.* 6: 2519-23 (1987). Other suitable selection markers are known as well.

Visible markers such as green florescent protein (GFP) may be used. Methods for identifying or selecting transformed plants based on the control of cell division have also been described. See John and Van Mellaert, WO 2000/052168, and Fabijansk et al., WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

According to a further aspect of the invention, nucleic acid constructs are provided that comprise a C3HC4 DNA sequence, as described above, under the control of a transcriptional initiation region operative in plants, such that the construct can generate RNA in plant cells. Preferably, the transcriptional initiation region is part of an organ or tissue-specific plant promoter, such as any of those described in the WO 2005/096805 published application. More preferably, the tissue-specific promoter, when operably linked to the C3HC4 DNA sequence, ensures transcription in specific cell types, tissues or organs such that cellulose synthesis can be specifically targeted without affecting other plant functions.

Transgenic plants of the invention can be characterized by increased cellulose content and/or by reduced lignin content. Increased cellulose content in the genetically engineered plant is preferably achieved via increase in C3HC4 expression in the plant tissues wherein cellulose deposition occurs. In a preferred embodiment, therefore, transgenic plants of the invention contain a nucleic acid construct comprising a cambium/xylem-preferred promoter such as those described in the '805 published international application cited above, operably linked to a gene encoding a C3HC4 protein, leading to increased expression in the plant vascular system of the C3HC4 gene, which in turn effects an increase in cellulose synthesis and deposition in those tissues without affecting other plant functions.

As noted, the cellulose content and related characteristics of plant parts may be modified by genetic engineering with a nucleic acid construct according to the invention. The invention also provides plant cells containing or genetically engineered with such constructs, plants derived there from having modified C3HC4 gene expression, and seeds of such plants.

Nucleic acid constructs according to the invention may comprise a base sequence of minimum length to generate mRNA and consequently a polypeptide retaining C3HC4 function. For convenience, it will generally be found suitable to use sequences between about 100 and about 1000 bases in length but there is no theoretical upper limit to the base sequence length. The preparation of such constructs is described in more detail below.

The isolated nucleic acid molecules of the invention may be incorporated into nucleic acid constructs, such that they are in operable linkage with a promoter. Preferably, the promoter is one known to operate in plant cells, and more preferably to be operable in cells of specific plant organs or tissues, such as roots, shoots, leaves, xylem, etc. The nucleic acid molecules of the invention may be placed in operable linkage with constitutive or inducible promoters. Alternatively, the nucleic acid molecules of the invention may be placed in operable linkage with promoters, which direct the expression of the downstream gene preferably, or specifically to an organ or tissue of the plant, such as xylem and cambium.

In addition, vascular system-specific, xylem-specific, or xylem preferred promoters may be useful to promote expression of the nucleic acid molecules of the invention specifically in vascular tissues, especially xylem tissue. The use of a constitutive promoter, in general, affects protein levels and functions in all parts of the plant, while use of a tissue-preferred promoter permits targeting of the modified gene expression to specific plant parts, leading to more controllable phenotypes. Thus, in applying the invention, it may be found convenient to use a promoter that will give expression during xylem development, whereby the proteins of the invention would only be overproduced in the organ(s) or tissue(s) or cell type(s) in which its action is required for the uses disclosed herein. Vascular tissue-specific, xylem-specific, vascular tissue-preferred and xylem-preferred promoters that could be used include, but are not limited to, the xylem-preferred coumarate-4-hydroxylase (C4H) gene promoter, the xylem-preferred tubulin (TUB) gene promoter and the xylem-preferred lipid transfer protein (LTP) gene promoter described in the aforementioned '805 published international application. The particular promoter selected should be capable of causing sufficient expression to result in the over-expression of the protein of the invention to modify the size of the xylem or to modify the chemical composition of the xylem of a plant or yet a combination of these effects.

Although the gene expression rate is mainly modulated by the promoter, improvement in expression may also be achieved by the identification and use of enhancer sequences, such as intronic portions of genes, which elevate the expression level of the nearby located genes in an independent manner orientation. In plants, the inclusion of some introns in gene constructs in a position between the promoter and the gene coding sequence leads to increases in mRNA and protein accumulation. Introns known to elevate expression in plants have been identified in maize genes, for example, hsp70, tubA1, Adh1, Sh1, UbH (Brown and Santino, U.S. Pat. Nos. 5,424,412 and 5,859,347; Jeon et al., 2000, *Plant Physiol.* 123: 1005-1014; Callis et al., 1987, *Genes Dev.* 1: 1183-1200; Vasil et al., 1989, *Plant Physiol.* 91: 1575-1579), and in dicotyledonous plant genes such as rbcS from petunia (Dean et al., 1989, *Plant Cell* 1: 201-208); ST-LS1 from potato (Leon et al., 1991, *Plant Physiol.* 95: 968-972) and UBQ3 (Norris et al., 1993, *Plant Mol. Biol.* 21: 895-906) and PAT1 from *Arabidopsis thaliana* (Rose and Last, 1997, *Plant J.* 11: 455-464).

In addition, the recombinant expression vector comprises a promoter functional in a plant cell, a nucleic acid molecule which is a homologue of the nucleotide sequences described above, and which encodes a polypeptide whose amino acid sequence contains regions that are at least 60% identical to the sequence set forth as SEQ ID. NO.: 2, as described above. More preferably, the nucleic acid molecule encodes a polypeptide whose amino acid sequence contains regions that are at least 70%, 80% or even 90% identical to the sequence above.

Constructs according to the invention may be used to genetically engineer any plant using any suitable technique. Both monocotyledonous and dicotyledonous angiosperm or gymnosperm plant cells may be genetically engineered in various ways known to the art. Klein et al., *Biotechnology* 4: 583-90 (1993); Bechtold et al., *C. R. Acad. Sci. Paris* 316: 1194-99 (1993); Bent et al., *Mol. Gen. Genet.* 204: 383-96 (1986); Paszowski et al., *EMBO J.* 3: 2717-2722 (1984); Sagi et al., *Plant Cell Rep.* 13: 262-66 (1994).

Plants for Genetic Engineering

The invention relates generally to transgenic plants which express genes or gene segments encoding the novel polypeptide compositions disclosed herein. As used herein, the term "transgenic plants" is intended to refer to plants that have incorporated nucleic acid sequences, including but not limited to genes which are perhaps not normally present, nucleic acid sequences not normally transcribed into RNA or translated into a protein ("expressed"), or any other genes or nucleic acid sequences which one desires to introduce into the plant, such as genes which may normally be present in the plant but which one desires to either genetically engineer or to have altered expression. It is contemplated that in some instances the genome of transgenic plants of the present invention will have been augmented through the stable introduction of a transgene. In other instances, however, the introduced gene or sequence will replace an endogenous sequence. A preferred gene, which may be introduced, includes but is not limited to the C3HC4 nucleic acid sequence from *Populus deltoides*.

Plants that can be engineered in accordance with the present invention include but are not limited to trees such as *Eucalyptus* species (*E. alba, E. albens, E. amygdalina, E. aromaphloia, E. baileyana, E. balladoniensis, E. bicostata, E. botryoides, E. brachyandra, E. brassiana, E. brevistylis, E. brockwayi, E. camaldulensis, E. ceracea, E. cloeziana, E. coccifera, E. cordata, E. cornuta, E. corticosa, E. crebra, E. croajingolensis, E. curtisii, E. dalrympleana, E. deglupta, E. delegatensis, E. delicata, E. diversicolor, E. diversifolia, E. dives, E. dolichocarpa, E. dundasii, E. dunnii, E. elata, E. erythrocorys, E. erythrophloia, E. eudesmoides, E. falcata, E. gamophylla, E. glaucina, E. globulus, E. globulus* subsp. *bicostata, E. globulus* subsp. *globulus, E. gongylocarpa, E. grandis, E. grandis×urophylla, E. guilfoylei, E. gunnii, E. hallii, E. houseana, E. jacksonii, E. lansdowneana, E. latisinensis, E. leucophloia, E. leucoxylon, E. lockyeri, E. lucasii, E. maidenii, E. marginata, E. megacarpa, E. melliodora, E. michaeliana, E. microcorys, E. microtheca, E. muelleriana, E. nitens, E. nitida, E. obliqua, E. obtusiflora, E. occidentalis, E. optima, E. ovata, E. pachyphylla, E. pauciflora, E. pellita, E. perriniana, E. petiolaris, E. pilularis, E. piperita, E. platyphylla, E. polyanthemos, E. populnea, E. preissiana, E. pseudoglobulus, E. pulchella, E. radiata, E. radiata* subsp. *radiata, E. regnans, E. risdonii, E. robertsonii, E. rodwayi, E. rubida, E. rubiginosa, E. saligna, E. salmonophloia, E. scoparia, E. sieberi, E. spathulata, E. staeri, E. stoatei, E. tenuipes, E. tenuiramis, E. tereticornis, E. tetragona, E. tetrodonta, E. tindaliae, E. torquata, E. umbra, E. urophylla, E. vernicosa, E. viminalis, E. wandoo, E. wetarensis, E. willisii, E. willisii* subsp. *falciformis, E. willisii* subsp. *willisii, E. woodwardii*), *Populus* species (*P. alba, P. alba×P. grandidentata, P. alba×P. tremula, P. alba×P. tremula* var. *glandulosa, P. alba×P. tremuloides, P. balsamifera, P. balsamifera* subsp. *trichocarpa, P. balsamifera* subsp. *trichocarpa×P. deltoides, P. ciliata, P. deltoides, P. euphratica, P. euramericana, P. kitakamiensis, P. lasiocarpa, P. laurifolia, P. maximowiczii, P. maximowiczii×P. balsamifera* subsp. *trichocarpa, P. nigra, P. sieboldii×P. grandidentata, P. suaveolens, P. szechuanica, P. tomentosa, P. tremula, P. tremula×P. tremuloides, P. tremuloides, P. wilsonii, P. canadensis, P. yunnanensis*), conifers such as loblolly pine (*Pinus taeda*), slash pine (*Pinus elliotii*), ponderosa pine (*Pinus ponderosa*), lodgepole pine (*Pinus*

*contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The present invention contemplates modification of fiber-producing plants as well, such as cotton (*Gossipium* spp.), flax (*Linum usitatissimum*), stinging nettle (*Urtica dioica*), hop (*Humulus lupulus*), lime trees (*Tilia cordata, T. x. europaea* and *T. platyphyllus*), spanish broom (*Spartium junceum*), ramie (*Boehmeria nivea*), paper mulberry (*Broussonetya papyrifera*), New Zealand flax (*Phormium tenax*), dogbane (*Apocynum cannabinum*), Iris species (*I. douglasiana, I. macrosiphon* and *I. purdyi*), milkweeds (*Asclepia* species), pineapple, banana and others. Also included are forage crops, such as alfalfa, lolium, festuca, and clover.

In this description, "plant" broadly indicates any cellulose-containing plant material that can be genetically manipulated, including but not being limited to differentiated or undifferentiated plant cells, protoplasts, whole plants, plant tissues, and plant organs, as well as any component of a plant such as a leaf, stem, root, bud, tuber, fruit, rhizome, and the like.

In the present description, "transgenic plant" refers to a plant that has incorporated a nucleic acid sequence, including but not limited to genes that are not normally present in a host plant genome, nucleic acid sequences not normally transcribed into RNA or translated into a protein, or any other genes or nucleic acid sequences that one desires to introduce into the wild-type plant, such as genes that normally may be present in the wild-type plant but that one desires either to genetically engineer or to have altered expression. The "transgenic plant" category includes both a primary transformant and a plant that includes a transformant in its lineage, e.g., by way of standard introgression or another breeding procedure. In contrast, a plant that is not genetically manipulated is a control plant and is referred to as a "non-transgenic" plant. Non-transgenic plant can be a plant whose genome is not modified by the introduction of a construct comprising the polynucleotide sequences or fragment thereof of the present invention. It can also be a plant regenerated from cultured cells or tissues without prior modification by the introduction of a construct comprising the polynucleotide sequence of the invention, or may comprise a homozygote recessive progeny (i.e., do not have any copy of the transgene) resulting from self-fertilization of a transgenic plant. As used herein, a "hybrid plant" refers to a plant or a part thereof resulting from a cross between two parent plants, wherein one parent is the genetically engineered plant of the invention. This can occur naturally by, for example, sexual reproduction, or artificially by, for example, in vitro nuclear fusion.

A transgenic plant of the present invention contains a nucleic acid sequence, as described herein that is expressed under the control of a promoter operative in plants, such that the plant is characterized, for example, by reduced lignin content and an increase in cellulose content.

Methods for Plant Genetic Engineering

Constructs according to the invention may be introduced into any plant cell, using a suitable engineering technique. Both monocotyledonous and dicotyledonous angiosperm or gymnosperm plant cells may be genetically engineered in various ways known to the art. For example, see Klein et al., 1993, *Biotechnology* 4: 583-590; Bechtold et al., 1993, *C. R. Acad. Sci. Paris* 316: 1194-1199; Koncz and Schell, 1986, *Mol. Gen. Genet.* 204: 383-396; Paszkowski et al., 1984, *EMBO J.* 3: 2717-2722; Sagi et al., 1994, *Plant Cell Rep.* 13: 262-266.

*Agrobacterium* species such as *A. tumefaciens* and *A. rhizogenes* can be used, for example, in accordance with Nagel et al., 1990, *Microbiol Lett* 67: 325. In brief, *Agrobacterium* may be transformed with a plant expression vector, for instance, via electroporation, after which the *Agrobacterium* is introduced to plant cells via, e.g., the well known leaf-disk method.

Additional methods for accomplishing this include, but are not limited to, transformation by *Rhizobium, Sinorhizobium* or *Mesorhizobium* (Broothaerts et al., 2005, *Nature* 433: 629-633), electroporation, particle gun bombardment, calcium phosphate precipitation, and polyethylene glycol fusion, transfer into germinating pollen grains, direct transformation (Lorz et al., 1985, *Mol. Genet.* 199: 179-82), and other known methods. If a selection marker, such as kanamycin resistance, is employed, it makes it easier to determine which cells have been successfully transformed.

The *Agrobacterium* transformation methods discussed above are known to be useful for transforming dicots. Additionally, de la Pena et al., 1987, *Nature* 325: 274-76; Rhodes et al., 1988, *Science* 240: 204-207; and Shimamoto et al., 1989, *Nature* 328: 274-76, disclose transforming cereal monocots using *Agrobacterium*. Also see Bechtold and Pelletier, 1998, *Methods Mol. Biol.* 82: 259-66, demonstrating the use of vacuum infiltration for *Agrobacterium*-mediated transformation.

The presence of a protein, polypeptide, or nucleic acid molecule in a particular cell can be measured to determine if, for example, a cell has been successfully genetically engineered. The ability to carry out such assay is well known and need not be reiterated here.

Quantifying Cellulose/Lignin Content

The phrase "increased cellulose content," employed here to describe a plant of the invention, refers to a quantitative augmentation in the amount of cellulose in the plant when compared to the amount of cellulose in a wild-type plant. A quantitative increase of cellulose can be assayed by several methods, as for example by quantification based on total sugars after acid hydrolysis of polysaccharides in stem milled wood. Chiang and Sarkanen, *Wood Sci. Technol.* 17: 217-26 (1983); Davis, *J. Wood Chem. Technol.* 18: 235-52 (1988).

The cellulose content in the engineered plant of the invention can be increased to levels of about 30% to about 50%, preferably about 25% to about 45%, even more preferably about 20% to about 40% of the cellulose content of the wild-type plant. A most preferred embodiment of the plant of the invention has a cellulose content of about 10% to about 15% of the wild-type cellulose content.

The phrases "reduced lignin content" and "decreased lignin content," used here to describe an aspect of a plant of the present invention, respectively refer to a quantitative reduction in the amount of lignin in the plant when compared to the amount of lignin in a wild-type or non-transformed plant. A quantitative reduction of lignin can be assayed by conventional methodology illustrated by the Klason lignin assay (Kirk et al., *Method in Enzymol.* 161: 87-101 (1988)) and the acetyl bromide assay of lignin (Iiyama et al., *Wood Sci. Technol.* 22: 271-80 (1988)).

The lignin content in an engineered plant of the invention can be reduced to levels of about 5% to about 90%, preferably about 10% to about 75%, even more preferably about 15% to about 65% by dry weight of the lignin content of the wild-type plant. A most preferred embodiment of the plant of the invention has a lignin content of about 20% to about 60% of the wild-type lignin content.

Provided below are examples of methodology for obtaining a *Populus deltoides* C3HC4 gene, as well as techniques for using *Agrobacterium* to introduce the target gene, to produce plant transformants are given below. They are meant to be mere examples and not a limitation of the present invention.

EXAMPLE 1

Expression Profile of Genes Preferably Expressed in Tension Wood, Reaction Wood and Normal Wood Expressed Sequence Tags (ESTs) from *Eucalyptus grandis×Eucalyptus urophylla* were clustered using the CAP3 program, as described by Huang and Madan, *Genome Res.* 9: 868-77 (1999), which is incorporated by reference. A group of 53,522 ESTs was obtained from libraries representing the following tissues: tension wood, reaction wood, and normal wood from field-grown eucalyptus trees (*Eucalyptus grandis×Eucalyptus urophylla*), 6.5 m in height. The set of clusters thus generated was searched for clusters composed of at least 90% of EST reads from libraries representing tension wood tissue. Additionally, the set of clusters was searched for clusters composed of at least three EST reads from tension wood tissue and, preferably, less than two reads from other libraries.

One cluster thus selected, composed of 14 EST reads from the tension wood cDNA library and 0 reads from other libraries (reaction and normal wood), represents a C3HC4 protein family member (FIG. 1).

The cluster selected using these parameters then was aligned, using the Blast-X algorithm with a cutoff e-value<=1e-5, see Altschul et al., *Nucleic Acids Res.* 25: 3389-402 (1997), to sequences from a curated *Populus* sp. database composed of sequences obtained from the JGI *Populus trichocarpa* v1.0 database (http://genome.jgi-psf.org/Poptr1/Poptr1.home.html). The comparison results were stored in a local database of *Populus* sequences. By this procedure, a cluster coding was retrieved for the C3HC4 protein that is orthologous to the one chosen from the *Eucalyptus* libraries. The sequence of the longest read in this cluster is set forth herein as SEQ ID NO.: 1, which codes for the polypeptide disclosed herein under SEQ ID NO: 2.

EXAMPLE 2

Isolation of a C3HC4 DNA Sequence from *Populus deltoides*

(a) Preparation of RNA from *Populus deltoides* cambium/xylem and cDNA Synthesis Bark was removed from stem cuttings of one-year-old *Populus deltoides* trees. The inner part of the stem, containing cambium, xylem and pith, was cut in small pieces, frozen in liquid nitrogen and used for RNA extraction using the cetyl-trimethyl-ammonium bromide (CTAB) extraction method (Aldrich and Cullis, Plant Mol. Biol. Report., 11:128-141 (1993)). A cDNA pool was used in RT-PCR experiments in which the isolated total RNA was used as template, and Superscript II reverse transcriptase (Invitrogen) and oligo (dT) primer were used to synthesize the first-strand cDNA. Double-stranded cDNA was obtained by the subsequent polymerase reaction, using gene-specific primers, as described below.

(b) Design of PCR Primers and RT-PCR Reaction.

Oligomers based on SEQ ID NO.: 1 were synthesized as primers for PCR, including either the region around the first ATG codon or around the termination codon of the main ORF encoding the polypeptide to amplify the entire coding region of the main ORF. The sequences of the primers are:

```
C3HC4NDE: Length: 30
catatgaata cgcggtaccc ctttccaatg    (SEQ ID NO:. 3)

C3HC4XBA: Length: 31
tctagactat ctctccaatc cttgtttaca g (SEQ ID NO: 4)
```

The cDNA pool obtained in (a) was used as the template in a PCR reaction with the primers of SEQ ID NOs: 5, 6, 7, and 8. The PCR involved 40 cycles of 1 minute at 94° C., 1 minute at 51° C., and 2 minutes at 72° C. followed by an extra step of elongation at 72° C. for 7 minutes. The PCR products were isolated by gel electrophoresis on 1.0% agarose followed by ethidium bromide staining of the electrophoresed gel and detection of amplified bands on a UV trans-illuminator. The detected amplified bands were verified and cut out of the agarose gel with a razor. The pieces of gel were transferred to 1.5 mL microtubes, and the DNA fragments were isolated and purified using a GFX PCR clean-up and gel band purification kit (Amersham). The recovered DNA fragments were subcloned in a commercially available cloning vector, transformed into *E. coli*, and then used to prepare plasmid DNA, which then was sequenced by the dideoxy method (Messing, *Methods in Enzymol.* 101, 20-78 (1983)) using standard methods. The nucleotide sequence SEQ ID NO. 1, which codes for the polypeptide disclosed herein under SEQ ID NO: 2, resulted.

EXAMPLE 3

Preparation of Transgenic *Nicotiana benthamiana* Plants

The nucleic acid molecules from *Populus deltoides* obtained in Example 2 above were introduced into a plant host to produce transgenic tobacco plants.

Figure 2:
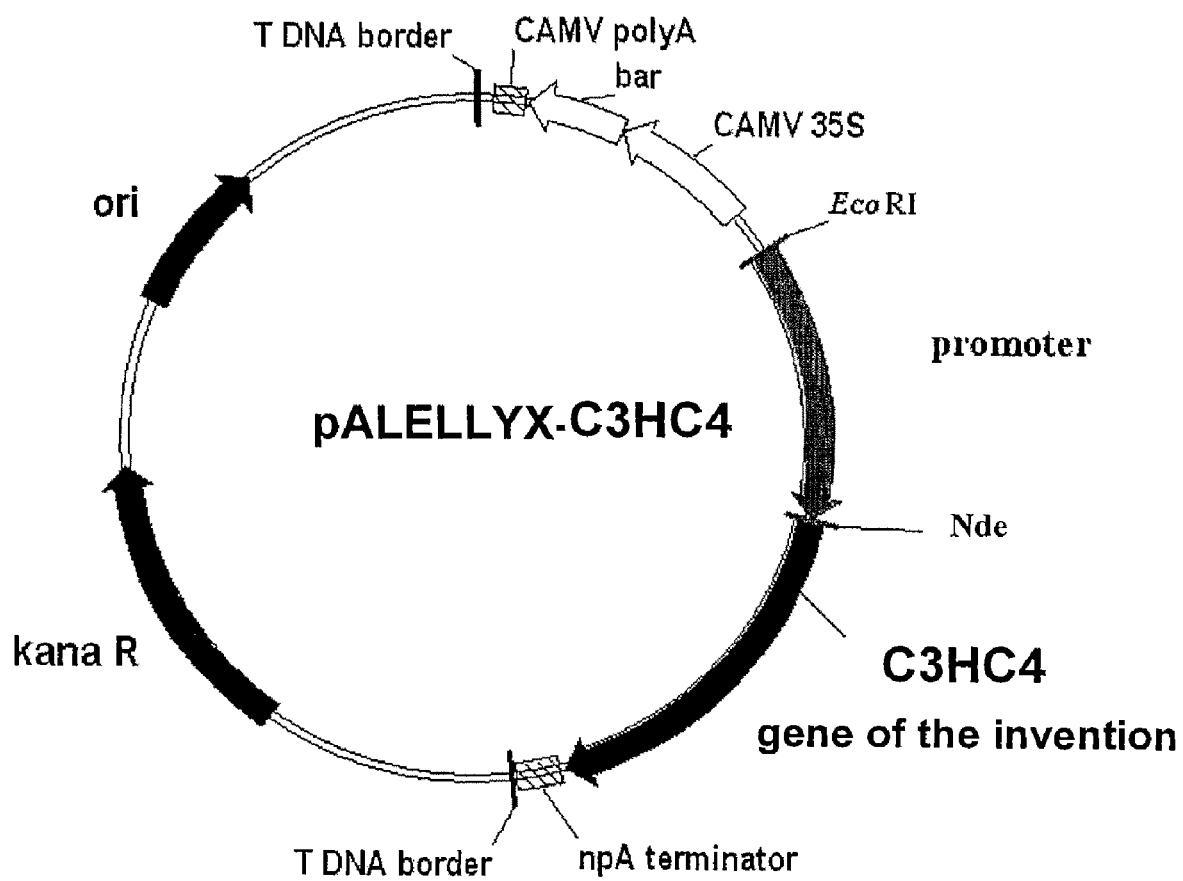
FIG. 2 schematically depicts plant expression plasmid vector pALELLYX-C3HC4 of the invention, which comprises a cambium/xylem-preferred promoter driving the expression of a C3HC4 nucleotide sequence of the invention.

The nucleic acid molecules isolated from *Populus deltoides* and obtained in Example 2 were cloned into an expression vector downstream of a xylem-preferred coumarate-4-hydroxylase gene (C4H) promoter (FIG. 2). The resulting expression constructs were amplified in *E. coli*, and then transformed by chemical transformation into *A. tumefaciens* LBA4404 strain.

*Agrobacterium*-mediated transformation of *Nicotiana benthamiana* was accomplished using the leaf disk method of Horsch et al., *Science* 227: 1229 (1985). In short, LBA4404 *Agrobacterium* strain was grown overnight until it reached mid-log phase growth. The cultures were diluted 1:10 in sterile water and co-cultivated for 20 min with leaf disks from sterile grown young *Nicotiana benthamiana* plants. These disks were incubated on Murashige-Skoog medium in the dark. After 48 hours, leaf disks were placed upside down on fresh plates of the same growth medium supplemented with 0.4 mg/L of indoleacetic acid (IAA), 2 mg/L benzyl-aminopurine (hOBAP), 1 mg/L Finale and 500 mg/L carbenicillin. When shoots formed, they were removed from the leaf disk and placed on fresh medium, supplemented with just 1 mg/L Finale. Shoots of primary transformants of *Nicotiana benthamiana*, heterozygous for the transgene, were allowed to root on Murashige and Skoog medium, and subsequently transferred to soil and grown in the greenhouse. The conditions (~50 pM/m2/sec of while light, 27° C.) were sufficient to identify those transgenic plants, which exhibited, altered xylem structure and/or xylem chemical composition, or a combination of these effects, according to the descriptions provided herein.

EXAMPLE 4

PCR Verification Foreign Gene Insertion into the Host Plant Genome

PCR was used to verify the integration of the gene construct in the genome of the transgenic plants. A pair of primers was synthesized to amplify a 400 bp DNA sequence from the selectable marker gene Bar. Additionally, another pair was synthesized to amplify the endogenous *Nicotiana benthamiana* chalcone synthase (CHS) gene. These primers sets are described in a published international application, WO 2006/096951.

```
Bar 35: Length: 20
tctaccatga gcccagaacg

Bar 36: Length: 23
aattcggggg atctggattt tag

CHS 150: Length: 24
gccagcccaa atccaagatt actc

CHS 151: Length: 23
aatgttagcc caacttcacg gag
```

The Bar primers were used to PCR-amplify part of the T-DNA portion of the expression construct containing a nucleic acid molecule of the invention, i.e., from genomic DNA of *Nicotiana benthamiana* transformants.

The PCR reaction mixture contained 100 ng genomic DNA of transformed plant, prepared using the cetyltrimethyl-ammonium bromide (CTAB) extraction method (Aldrich and Cullis, *Plant Mol. Biol. Report* 11: 128-41 (1993)), 0.2 µM of each primer for the Bar gene, 0.2 µM of each primer for the endogenous CHS control gene, 100 µM of each deoxyribonucleotide triphosphate, 1×PCR buffer and 2.5 Units of AmpliTaq DNA polymerase (Applied Biosystems) in a total volume of 50 µL. The cycling parameters were as follows: 94° C. for 1 minute, 57° C. for 1 minute and 72° C. for 1 minute, for 40 cycles, with 5 minutes at 72° C. extension. The PCR products were electrophoresed on a 1% agarose gel.

EXAMPLE 5

Determination of Transgene Expression Levels in Transgenic Plants

Semi-quantitative RT-PCR was used to detect the accumulation of *Populus deltoides* C3HC4 transcripts in stem tissue of the transgenic plants. Total RNA was isolated from stem cuts of 4-months old transgenic *Nicotiana* T0 plants using the CTAB method (Aldrich and Cullis, *Plant Mol. Biol. Report.* 11:128-141 (1993)). cDNA was synthesized from 500 ng of total RNA using Superscript II RNase H-RT (Invitrogen, USA). The primers described above were used along with primers for the constitutive gene encoding chalcone synthase (CHS) as internal control to normalize the quantity of total RNA used in each sample. The PCR was done with a 12.5-fold dilution of the first-strand cDNA under the following conditions: 94° C. for 3 minutes and 27 cycles of 94° C. for 1 minute, 51° C. for 1 minute, and 72° C. for 1 minute and 30 seconds.

The foregoing disclosure and examples describe various features of the invention, which essentially entail the isolation and cloning of nucleic acid molecules that encode a member of the C3HC4 protein family and that are useful in producing genetically engineered plants. Recombinant plants which have been transformed or transfected with such isolated nucleic acid molecule may exhibit quantitative alteration in cellulose and/or lignin content.

EXAMPLE 6

Histochemical Analysis of Transgenic Plants

Stems of transgenic *Nicotiana* and control non-transgenic plants were sectioned and fixed in 4% paraformaldehyde for 24 hours. Fixed tissues then were sectioned on a microtome (Leica RM2255) and subsequently stained with astra blue/saffranin. The histologically stained sections were observed under a Leica DM1L inverted microscope using bright- and dark-field illumination.

EXAMPLE 7

Figure 3:
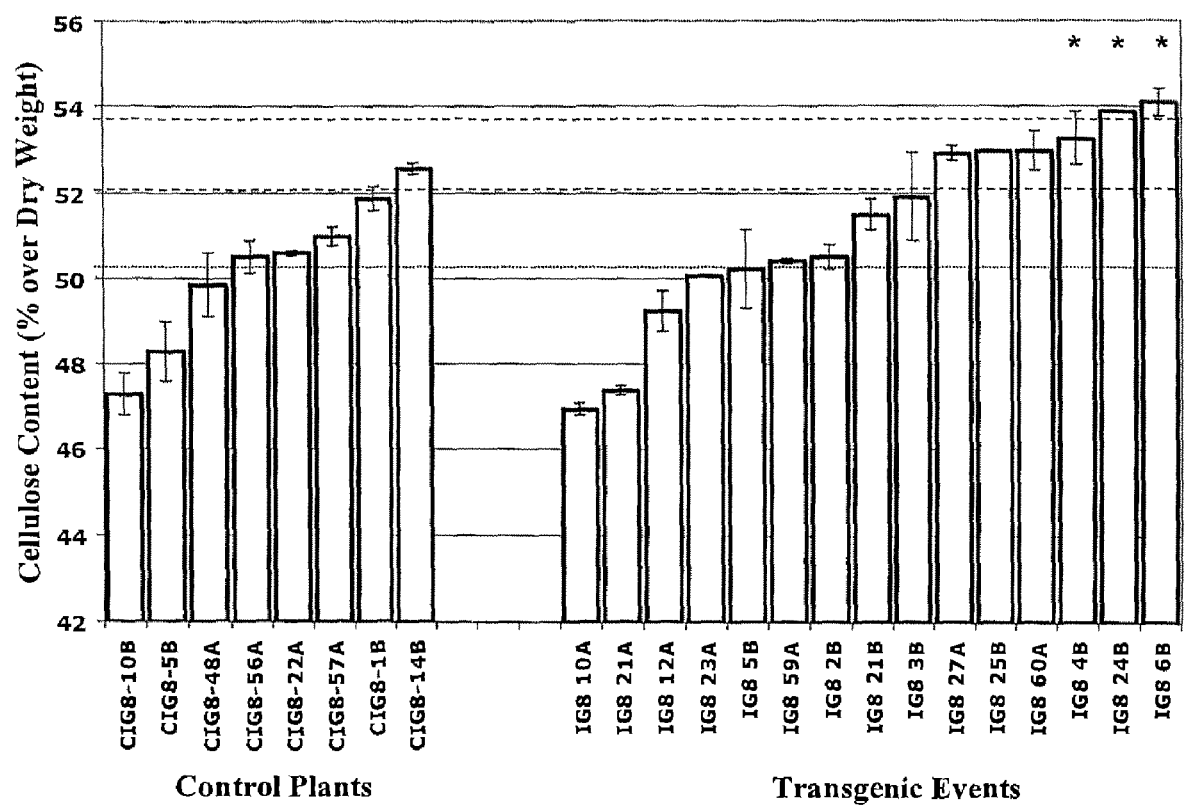
FIG. 3 shows the cellulose content of several transgenic lines, transformed with pALELLYX-C3HC4, and respective control non-transgenic plants. Asterisk denotes statistically significant higher mean cellulose content values.

Increase in Cellulose Content in Transgenic Plants Over-Expressing C3HC4 in Vascular Tissues The main stems of Nicotiana transgenic events transformed with constructs comprising the *Populus deltoides* C3HC4 gene under the control of the xylem-preferred *Populus deltoides* C4H promoter and non-transgenic control plants were collected and air-dried for two weeks. Dried stems were cut in pieces and powdered on a knife mill using a 30-mesh sieve. Stem powder samples were then subjected to chemical analyses to determine cellulose and lignin content. In brief, cellulose and hemicellulose contents were determined based on the total sugars after acid hydrolysis of these polysaccharides extracted from the stem. The milled stems were vacuum-dried at 45° C. and hydrolyzed with $H_2SO_4$. Following high-pH anion-exchange chromatography, glucan and other polysaccharides (hemicelluloses) were quantified based on hydrolysate composition. Chiang and Sarkanen (1983) and Davis (1988), supra. Three of the C3HC4 transgenic events, known to express the transgene according to procedure detailed in Example 5, showed a statistically significant increase in cellulose content (FIG. 3). Transgenic event 6B exhibits 54.09% cellulose as compared to 50.00% in control non-transgenic plants, representing a significant increase of 8.18% in cellulose content ($P \leq 0.05$, t-test). Transgenic event 24B exhibits 53.90% cellulose, compared to 50.00% in control plants, representing 7.80% increase in cellulose content (FIG. 3; $P \leq 0.05$, t-test). Transgenic event 4B exhibits 53.26% cellulose content as compared to 50.00% in control non-transgenic plants, representing 6.52% increase in cellulose content (FIG. 3; $P \leq 0.05$, t-test).

After grown to maturity, the T0 events were selfed to generate T1 lines. Here we present the results concerning three events that have their T1 generation analyzed.

Figure 4:
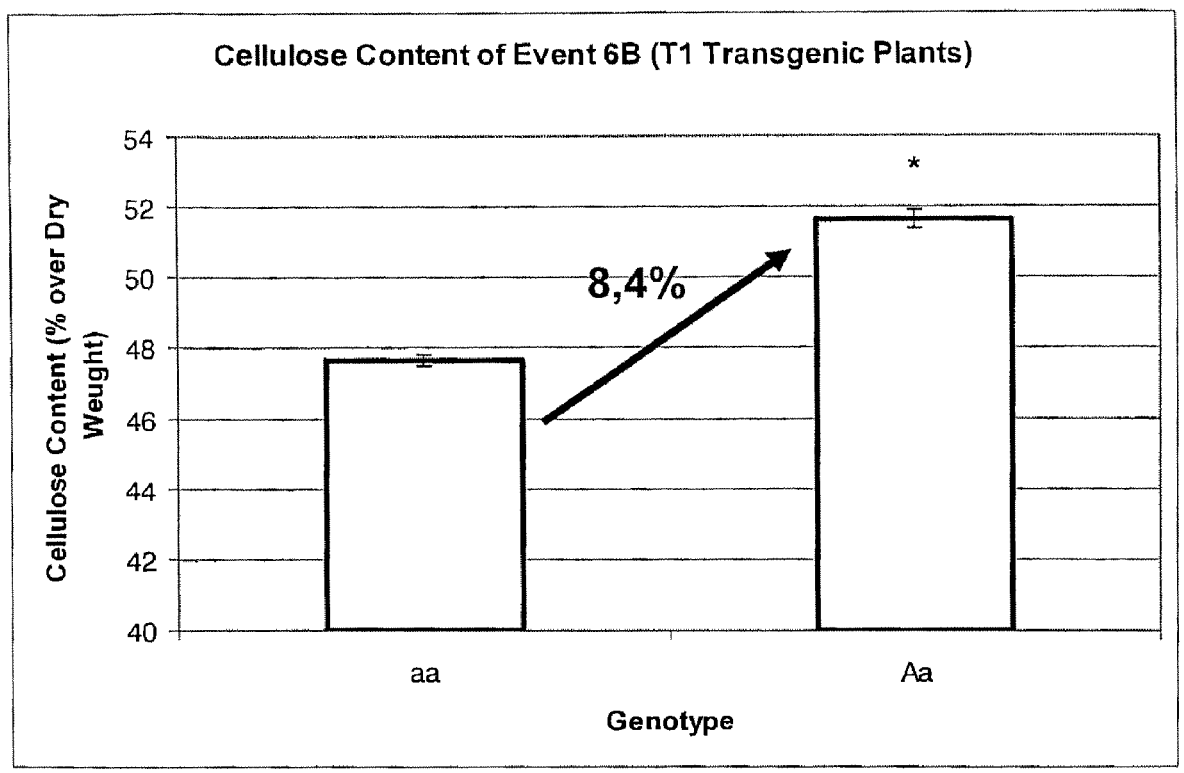
FIG. 4 shows the cellulose content of two genotypes of a T1 transgenic plant (line 6B) transformed with pALELLYX-C3HC4. Asterisk denotes statistically significant higher mean cellulose content values ($P<0.05$, t-test).
Figure 5:
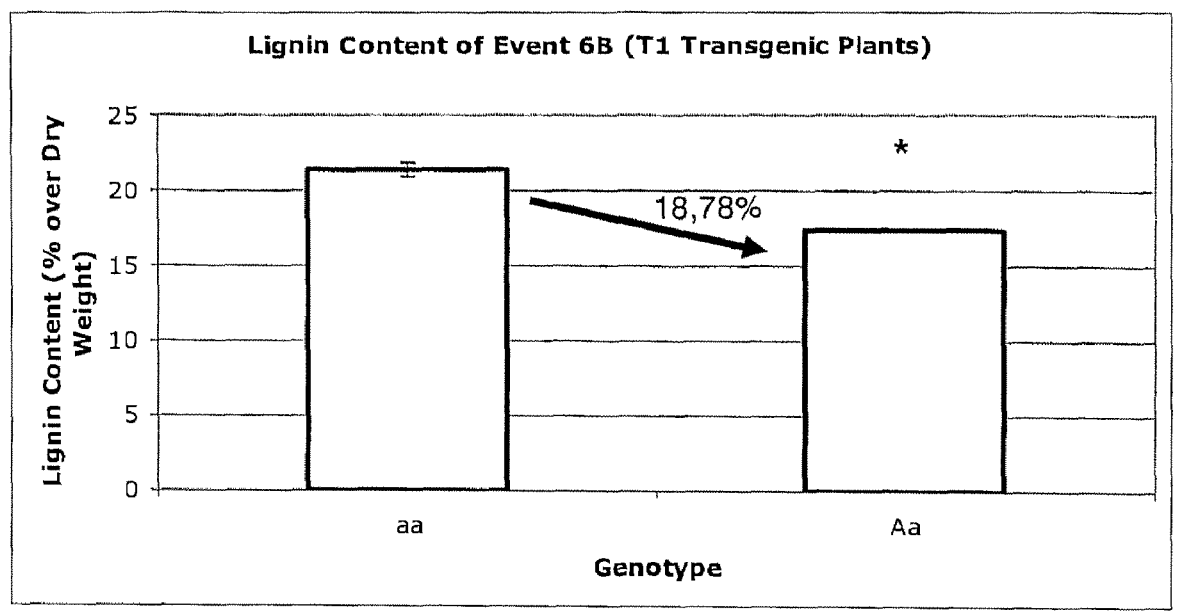
FIG. 5 shows the lignin content of two genotypes of a T1 transgenic plant (line 6B) transformed with the plant expression plasmidial vector pALELLYX-C3HC4 of the invention. Asterisk denotes statistically significant lower mean lignin content values ($P<0.05$, t-test).

Analysis of the T1 population from event 6B indicated that the homozygous dominant condition for the C3HC4 gene is lethal, since no homozygous dominant plant was detected in the segregant population. Plant development probably was affected. Nevertheless, plants that are hemizygous for the C3HC4 gene presented a significant increase of 8.4% in cellulose content (P<0.05, t-test), when compared to homozygous recessive plants (FIG. 4). They also showed a reduction of 18% in their lignin content (P<0.05, t-test), when compared to homozygous recessive plants (FIG. 5).

Figure 6:
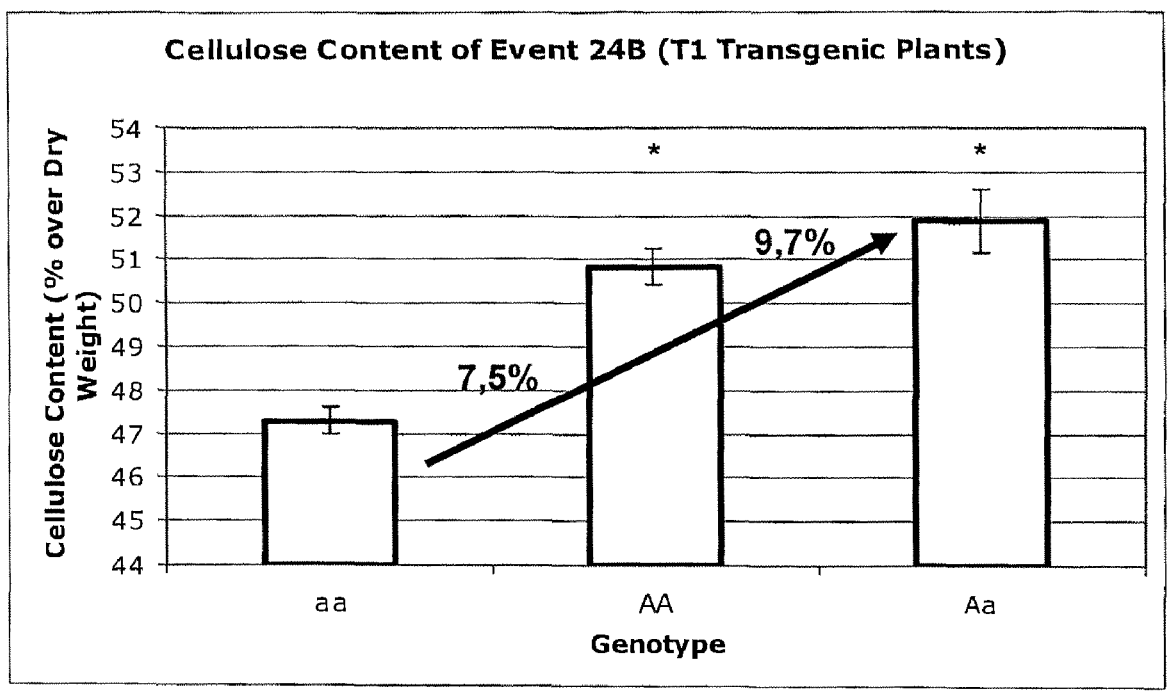
FIG. 6 shows the cellulose content of three genotypes of a T1 transgenic plant (line 24B) transformed with the plant expression plasmidial vector pALELLYX-C3HC4 of the invention. Asterisk denotes statistically significant higher mean cellulose content values ($P<0.05$, t-test).
Figure 7:
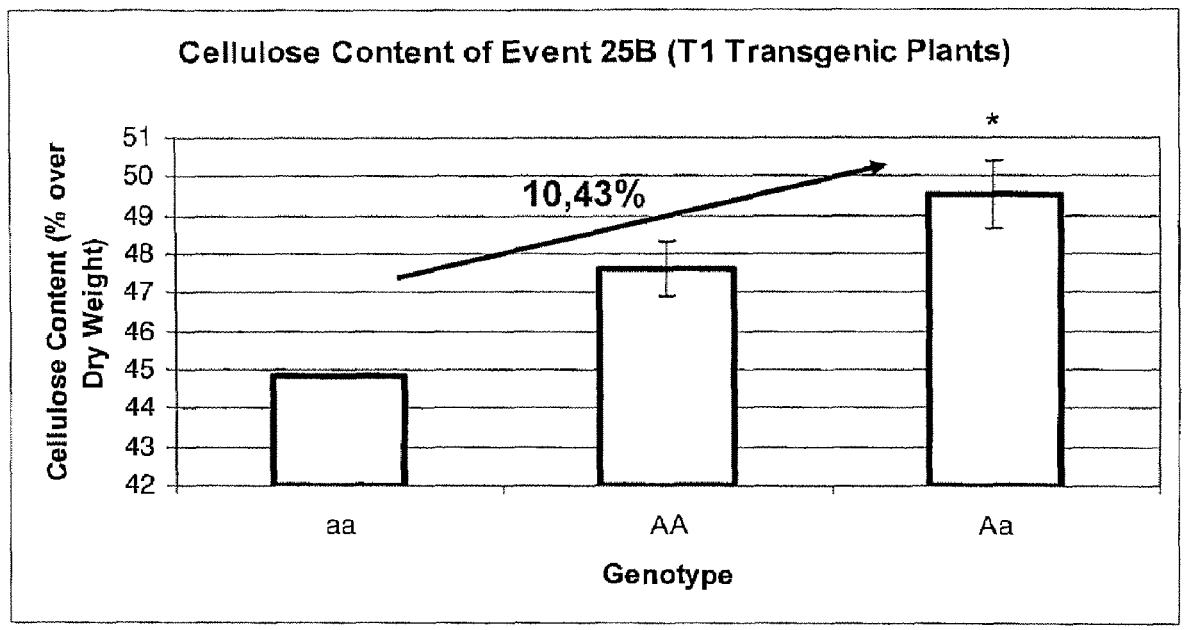
FIG. 7 shows the cellulose content of three genotypes of a T1 transgenic plant (line 25B) transformed with the plant expression plasmidial vector pALELLYX-C3HC4 of the invention. Asterisk denotes statistically significant higher values of mean cellulose content ($P<0.05$, t-test).

In the segregant population of events 24B and 25B, it was possible to identify homozygous dominant plants. But the higher increase in cellulose content was observed in the group of hemizygous plants, when compared to the homozygous recessive plants. Hemizygous plants from event 24B showed an increase of 9.7% in cellulose content and homozygous dominant plants presented an increase of 7.5% in cellulose content as compared to homozygous recessive plants (FIG. 6; $P \leq 0.05$, t-test). Hemizygous plants from event 25B showed an increase of 10.4%, compared to the group of homozygous recessive plants (FIG. 7; $P \leq 0.05$, t-test). No significant alteration in lignin content was observed for these two events.

What is claimed is:

1. An isolated nucleic acid sequence comprising a sequence selected from the group consisting of:
   (a) a nucleic acid sequence set forth in SEQ ID NO: 1, or the complement strand thereof;
   (b) a nucleic acid sequence encoding the amino acid sequence set forth in SEQ ID NO: 2;
   (c) a nucleic acid sequence capable of hybridizing under the conditions of: 3.5×SSC, 1×Denhardt's solution, 25 mM sodium phosphate buffer (pH 7.0), 0.5% SDS, and 2 mM EDTA for 18 hours at 65° C. followed by 4 washes at 65° C. for 20 minutes in 2×SSC, 0.1% SDS, and a final wash of 20 minutes in 0.1×SSC, 0.1% SDS, with a nucleic acid sequence of (a) or (b), wherein said hybridizing sequence encodes a C3HC4 polypeptide that, when overexpressed, results in an increase in the cellulose content and/or in a decrease in the lignin content of a plant, said C3CH4 polypeptide comprising a C3HC4 consensus motif; and
   (d) a nucleic acid sequence that encodes a C3HC4 polypeptide amino acid sequence which is at least 95% or more identical to SEQ ID NO: 2, the over-expression of which results in an increase in the cellulose content and/or in a decrease in the lignin content of a plant, said C3HC4 polypeptide comprising a C3HC4 consensus motif.

2. An isolated C3HC4 protein selected from the group consisting of:
   (a) a polypeptide set forth in SEQ ID NO: 2; and
   (b) a polypeptide with an amino acid sequence comprising a C3HC4 consensus motif and having at least 95% or more sequence identity to the amino acid sequence set forth in SEQ ID NO: 2, the over-expression of which results in an increase in the cellulose content and/or in a decrease in the lignin content of a plant.

3. A nucleic acid construct comprising the isolated nucleic acid sequence of claim 1 operably linked to one or more suitable promoters that drive the expression of the nucleic acid sequence.

4. The nucleic acid construct of claim 3, wherein the promoter is a xylem-preferred promoter.

5. The nucleic acid construct of claim 4, wherein said xylem-preferred promoter is selected from the group consisting of TUB gene promoter, SuSy gene promoter, COMT gene promoter, and C4H gene promoter.

6. A plant cell comprising the nucleic acid construct of claim 3.

7. A transgenic plant generated from the plant cell of claim 6, wherein said plant has altered cellulose and/or lignin content compared to a non-transgenic plant of the same species.

8. The plant cell of claim 6, wherein said promoter is a xylem-preferred promoter.

9. The plant cell of claim 8, wherein said xylem-preferred promoter is selected from the group consisting of TUB gene promoter, SuSy gene promoter, COMT gene promoter, and C4H gene promoter.

10. The transgenic plant of claim 7, wherein said plant is a dicotyledon plant.

11. The transgenic plant of claim 7, wherein said plant is a monocotyledon plant.

12. The transgenic plant of claim 7, wherein said plant is a gymnosperm.

13. The transgenic plant of claim 7, wherein said plant is a hardwood tree.

14. The transgenic plant of claim 13, wherein said hardwood tree is an *Eucalyptus* plant.

15. The transgenic plant of claim 13, wherein said hardwood tree is a *Populus* plant.

16. The *Populus* plant of claim 11, wherein said plant is a *Pinus* plant.

17. A part of the transgenic plant of claim 7 selected from the group consisting of a leaf, a stem, a flower, an ovary, a fruit, a seed and a callus that comprises the nucleic acid construct of claim 3.

18. Progeny of the transgenic plant of claim 7 that comprises the nucleic acid construct of claim 3.

19. The progeny of claim 18, wherein said progeny is a hybrid plant.

20. A method for altering the cellulose and/or lignin content in a plant, comprising
   (a) introducing into an isolated plant cell a nucleic acid construct comprising the isolated nucleic acid sequence of claim 1, operably linked to one or more suitable promoters that drive the expression of the nucleic acid sequence; and
   (b) culturing said plant cell under conditions that promote growth of a plant, wherein said plant over-expresses the C3HC4 protein and has increased cellulose and/or reduced lignin content compared to a non-transgenic plant of the same species.

21. The method of claim 20, wherein the promoter is a xylem-preferred promoter.

22. The method of claim 21, wherein the xylem-preferred promoter is selected from the group consisting of TUB gene promoter, SuSy gene promoter, COMT gene promoter, and C4H gene promoter.

23. An isolated C3HC4 protein comprising a polypeptide with an amino acid sequence having at least 95% or more sequence identity to the amino acid sequence set forth in SEQ ID NO: 2, the over-expression of which results in an increase in the cellulose content and/or in a decrease in the lignin content of a plant, the amino acid sequence comprising a C3HC4 consensus motif.

24. An isolated nucleic acid sequence comprising a nucleic acid sequence encoding the amino acid sequence set forth in SEQ ID NO: 2.

* * * * *

SEQUENCE LISTING

<160> NUMBER OF SEQ ID NOS: 8

<210> SEQ ID NO 1
<211> LENGTH: 1026
<212> TYPE: DNA
<213> ORGANISM: Populus deltoides
<220> FEATURE:
<221> NAME/KEY: CDS
<222> LOCATION: (1)..(1023)
<223> OTHER INFORMATION: Populus deltoides C3HC4 protein, cDNA clone

<400> SEQUENCE: 1

```
atg aat acg cgg tac ccc ttt cca atg aat tca ttc tgt ggt tca agt      48
Met Asn Thr Arg Tyr Pro Phe Pro Met Asn Ser Phe Cys Gly Ser Ser
1               5                   10                  15 cct gca gca tct cca gca gga gaa gag cgt gga act gtg tct ctc aga      96
Pro Ala Ala Ser Pro Ala Gly Glu Glu Arg Gly Thr Val Ser Leu Arg
                20                  25                  30 aac agg tct gct cgc act ccc act tcg tcc tta ttg gta aga aca gcg     144
Asn Arg Ser Ala Arg Thr Pro Thr Ser Ser Leu Leu Val Arg Thr Ala
            35                  40                  45 atg aga ata tct aga gca aga tgg ttc acc ttc ttg aga aga gta ttc     192
Met Arg Ile Ser Arg Ala Arg Trp Phe Thr Phe Leu Arg Arg Val Phe
        50                  55                  60 cac tac cag aat ggc tca agg tct aat ctt ggg tct aat cct ttc aac     240
His Tyr Gln Asn Gly Ser Arg Ser Asn Leu Gly Ser Asn Pro Phe Asn
65                  70                  75                  80 tcc agc act tgg atg atg ctg gag ttt gta gct ttg gtc ctt caa ata     288
Ser Ser Thr Trp Met Met Leu Glu Phe Val Ala Leu Val Leu Gln Ile
                85                  90                  95 agt att acc atg ttc acc ctg gct att tcc aag gca gag aag cca gtt     336
Ser Ile Thr Met Phe Thr Leu Ala Ile Ser Lys Ala Glu Lys Pro Val
                100                 105                 110 tgg cct gtg aga ata tgg att att ggc tat aat att ggt tgt gtc ctt     384
Trp Pro Val Arg Ile Trp Ile Ile Gly Tyr Asn Ile Gly Cys Val Leu
            115                 120                 125 agt ctg ctg ctg ttc tat ggg cga tac cgg caa att aac acg act caa     432
Ser Leu Leu Leu Phe Tyr Gly Arg Tyr Arg Gln Ile Asn Thr Thr Gln
        130                 135                 140 ggc gat ggt ttt ggc cta cct gat ttg gaa caa cag agg ggc agt gag     480
Gly Asp Gly Phe Gly Leu Pro Asp Leu Glu Gln Gln Arg Gly Ser Glu
145                 150                 155                 160 gaa tcc agt gta tgc agg tgc tca att ttg atg cac aag tgc cgg act     528
Glu Ser Ser Val Cys Arg Cys Ser Ile Leu Met His Lys Cys Arg Thr
                165                 170                 175 tca ctc gag ctc ttc ttt gca ata tgg ttt gtg atg ggt aat gtt tgg     576
Ser Leu Glu Leu Phe Phe Ala Ile Trp Phe Val Met Gly Asn Val Trp
                180                 185                 190 gtc ttt gat tct cgc ttt gga tcc tac cac cgt gct cca aaa ctc cat     624
Val Phe Asp Ser Arg Phe Gly Ser Tyr His Arg Ala Pro Lys Leu His
            195                 200                 205 gtg cta tgc atc tct cta ctt gcc tgg aat gct ctc agt tac tcc ttc     672
Val Leu Cys Ile Ser Leu Leu Ala Trp Asn Ala Leu Ser Tyr Ser Phe
        210                 215                 220
```

-continued

```
cca ttt ctc ttg ttt cta ctc tta tgt tgt tgc gtg cca ctc att agc        720
Pro Phe Leu Leu Phe Leu Leu Leu Cys Cys Cys Val Pro Leu Ile Ser
225                 230                 235                 240 act gtc ctt ggt tac aac atg aac atg ggt tct gcc gag aga ggg gct        768
Thr Val Leu Gly Tyr Asn Met Asn Met Gly Ser Ala Glu Arg Gly Ala
                245                 250                 255 tcc gac gat caa atc tcc agt cta cca agt tgg agg tac aaa gca gct        816
Ser Asp Asp Gln Ile Ser Ser Leu Pro Ser Trp Arg Tyr Lys Ala Ala
            260                 265                 270 gac acc aac tcg gag ttt cgc aat aat gct gac tgc aat tca acc att        864
Asp Thr Asn Ser Glu Phe Arg Asn Asn Ala Asp Cys Asn Ser Thr Ile
        275                 280                 285 gca agt gaa gat ctg gaa tgt tgt atc tgc cta gcc aag tat aaa gac        912
Ala Ser Glu Asp Leu Glu Cys Cys Ile Cys Leu Ala Lys Tyr Lys Asp
    290                 295                 300 aaa gaa gaa gtt agg aaa ttg cca tgt tcc cat atg ttc cac ctc aag        960
Lys Glu Glu Val Arg Lys Leu Pro Cys Ser His Met Phe His Leu Lys
305                 310                 315                 320 tgt gta gat caa tgg ctt cga att ata tcc tgc tgc cct ctc tgt aaa       1008
Cys Val Asp Gln Trp Leu Arg Ile Ile Ser Cys Cys Pro Leu Cys Lys
                325                 330                 335 caa gga ttg gag aga tag                                               1026
Gln Gly Leu Glu Arg
                340
```

<210> SEQ ID NO 2
<211> LENGTH: 341
<212> TYPE: PRT
<213> ORGANISM: Populus deltoides

<400> SEQUENCE: 2

Met Asn Thr Arg Tyr Pro Phe Pro Met Asn Ser Phe Cys Gly Ser Ser
1               5                   10                  15

Pro Ala Ala Ser Pro Ala Gly Glu Glu Arg Gly Thr Val Ser Leu Arg
            20                  25                  30

Asn Arg Ser Ala Arg Thr Pro Thr Ser Ser Leu Leu Val Arg Thr Ala
        35                  40                  45

Met Arg Ile Ser Arg Ala Arg Trp Phe Thr Phe Leu Arg Val Phe
    50                  55                  60

His Tyr Gln Asn Gly Ser Arg Ser Asn Leu Gly Ser Asn Pro Phe Asn
65                  70                  75                  80

Ser Ser Thr Trp Met Met Leu Glu Phe Val Ala Leu Val Leu Gln Ile
                85                  90                  95

Ser Ile Thr Met Phe Thr Leu Ala Ile Ser Lys Ala Glu Lys Pro Val
            100                 105                 110

Trp Pro Val Arg Ile Trp Ile Ile Gly Tyr Asn Ile Gly Cys Val Leu
        115                 120                 125

Ser Leu Leu Leu Phe Tyr Gly Arg Tyr Arg Gln Ile Asn Thr Thr Gln
    130                 135                 140

Gly Asp Gly Phe Gly Leu Pro Asp Leu Glu Gln Gln Arg Gly Ser Glu
145                 150                 155                 160

Glu Ser Ser Val Cys Arg Cys Ser Ile Leu Met His Lys Cys Arg Thr
                165                 170                 175

Ser Leu Glu Leu Phe Phe Ala Ile Trp Phe Val Met Gly Asn Val Trp
            180                 185                 190

Val Phe Asp Ser Arg Phe Gly Ser Tyr His Arg Ala Pro Lys Leu His
        195                 200                 205

Val Leu Cys Ile Ser Leu Leu Ala Trp Asn Ala Leu Ser Tyr Ser Phe

```
                    210                 215                 220
Pro Phe Leu Leu Phe Leu Leu Cys Cys Val Pro Leu Ile Ser
225                 230                 235                 240

Thr Val Leu Gly Tyr Asn Met Asn Met Gly Ser Ala Glu Arg Gly Ala
                245                 250                 255

Ser Asp Asp Gln Ile Ser Ser Leu Pro Ser Trp Arg Tyr Lys Ala Ala
                260                 265                 270

Asp Thr Asn Ser Glu Phe Arg Asn Asn Ala Asp Cys Asn Ser Thr Ile
                275                 280                 285

Ala Ser Glu Asp Leu Glu Cys Cys Ile Cys Leu Ala Lys Tyr Lys Asp
            290                 295                 300

Lys Glu Glu Val Arg Lys Leu Pro Cys Ser His Met Phe His Leu Lys
305                 310                 315                 320

Cys Val Asp Gln Trp Leu Arg Ile Ile Ser Cys Cys Pro Leu Cys Lys
                325                 330                 335

Gln Gly Leu Glu Arg
            340

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      C3HC4NDE primer

<400> SEQUENCE: 3
catatgaata cgcggtaccc ctttccaatg                                  30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      C3HC4XBA primer

<400> SEQUENCE: 4
tctagactat ctctccaatc cttgtttaca g                                31

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Bar 35 primer

<400> SEQUENCE: 5
tctaccatga gcccagaacg                                             20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      Bar 36 primer

<400> SEQUENCE: 6
aattcggggg atctggattt tag                                         23

<210> SEQ ID NO 7
```

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      CHS 150 primer

<400> SEQUENCE: 7
gccagcccaa atccaagatt actc                                          24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      CHS 151 primer

<400> SEQUENCE: 8
aatgttagcc caacttcacg gag                                           23
```